US011318036B2

(12) United States Patent
Cook et al.

(10) Patent No.: US 11,318,036 B2
(45) Date of Patent: May 3, 2022

(54) BRACE AND A METHOD OF FITTING A BRACE

(71) Applicant: The SpineCorporation Limited, Derbyshire (GB)

(72) Inventors: Timothy James Cook, Derbyshire (GB); Andrew James Mills, Derbyshire (GB)

(73) Assignee: The SpineCorporation Limited, Derbyshire (GB)

( * ) Notice: Subject to any disclaimer, the term of this patent is extended or adjusted under 35 U.S.C. 154(b) by 519 days.

(21) Appl. No.: 16/312,194

(22) PCT Filed: Jul. 6, 2017

(86) PCT No.: PCT/GB2017/051987
§ 371 (c)(1),
(2) Date: Dec. 20, 2018

(87) PCT Pub. No.: WO2018/007816
PCT Pub. Date: Jan. 11, 2018

(65) Prior Publication Data
US 2019/0231575 A1    Aug. 1, 2019

(30) Foreign Application Priority Data

Jul. 6, 2016  (GB) ..................................... 1611789

(51) Int. Cl.
*A61F 5/00* (2006.01)
*A61F 5/02* (2006.01)
(52) U.S. Cl.
CPC .................................... *A61F 5/028* (2013.01)
(58) Field of Classification Search
CPC .......... A61F 5/058; A61F 5/028; A61F 5/024; A61F 5/026; A61F 5/0193
(Continued)

(56) References Cited

U.S. PATENT DOCUMENTS 903,403   A  *  11/1908  Quick et al. ............ A61F 5/028
                                                    2/44
2,828,737 A  *   4/1958  Hale ....................... A61F 5/028
                                                   602/19
(Continued)

FOREIGN PATENT DOCUMENTS

EP    2502608 A1    9/2012
RU    2223069 C1    2/2004
(Continued)

OTHER PUBLICATIONS

International Search Report and Written Opinion, corresponding International Application No. PCT/GB2017/051987, dated Dec. 12, 2017.
(Continued)

*Primary Examiner* — Kim M Lewis
(74) *Attorney, Agent, or Firm* — Marshall, Gerstein & Borun LLP

(57) ABSTRACT

A brace (101, 101A) and method (1300, 1400) of fitting a brace to a person are disclosed. The brace includes a belt assembly (102) for location around a body of a user and a strut (103) having a first end (104) configured to be secured by the belt assembly (102) and an anchoring location (105) spaced from the belt assembly (102). The brace also includes a first strap (106) for applying a force to the body of the user, a first anchor means (107) configured to retain a first part of the first strap (106) at the anchoring location (105) on the strut (103) and a second anchor means (108) configured to retain a second part of the first strap (106) at a second anchor location (109) to enable tension to be provided in the first strap.

17 Claims, 13 Drawing Sheets

(58) Field of Classification Search
USPC .......................................................... 602/24
See application file for complete search history.

(56) References Cited

U.S. PATENT DOCUMENTS

| | | | | |
|---|---|---|---|---|
| 4,696,291 | A * | 9/1987 | Tyo | ........................ A61F 5/028 602/19 |
| 5,135,470 | A | 8/1992 | Reeves | |
| 5,599,286 | A * | 2/1997 | Labelle | ................... A61F 5/024 128/875 |
| 6,063,047 | A | 5/2000 | Minne | |
| 2006/0282032 | A1* | 12/2006 | Smith | ..................... A61F 5/028 602/19 |
| 2010/0217166 | A1* | 8/2010 | Mills | ........................ A61F 5/024 602/19 |
| 2012/0059297 | A1* | 3/2012 | Newkirk | ................. A61F 5/028 602/19 |
| 2012/0095379 | A1* | 4/2012 | Hama | ................... A61F 5/0193 602/23 |
| 2013/0184625 | A1* | 7/2013 | Ingimundarson | ....... A61F 5/028 602/19 |
| 2013/0283492 | A1* | 10/2013 | Ernst, Jr. | .................. A45F 3/08 2/44 |
| 2014/0018715 | A1 | 1/2014 | Ingimundarson et al. | |
| 2014/0024973 | A1* | 1/2014 | Pettit | .................... A61B 5/7275 600/595 |
| 2014/0030187 | A1* | 1/2014 | Weichert | ............... C07F 13/005 424/1.77 |
| 2014/0100501 | A1* | 4/2014 | Burke | ..................... A61F 5/028 602/19 |
| 2014/0330187 | A1 | 11/2014 | Perez et al. | |
| 2014/0371646 | A1* | 12/2014 | Kozersky | ................ A61F 5/028 602/19 |
| 2019/0021895 | A1* | 1/2019 | Breuil | ..................... A61F 5/028 |
| 2019/0029866 | A1* | 1/2019 | Stier | ....................... A61F 5/028 |

FOREIGN PATENT DOCUMENTS

| | | |
|---|---|---|
| RU | 2002123690 A | 3/2004 |
| RU | 2317800 C1 | 2/2008 |
| WO | WO-2014/182742 A1 | 11/2014 |

OTHER PUBLICATIONS

United Kingdom Search Report for GB Application No. 1611789.7, dated Dec. 22, 2016.

* cited by examiner

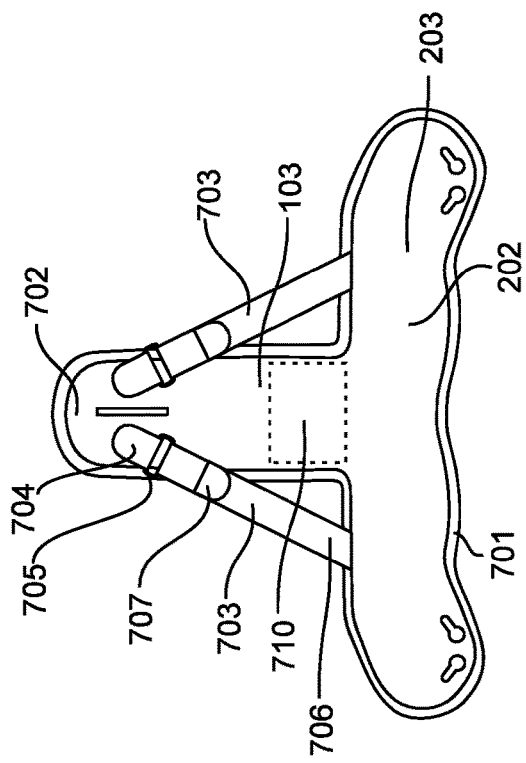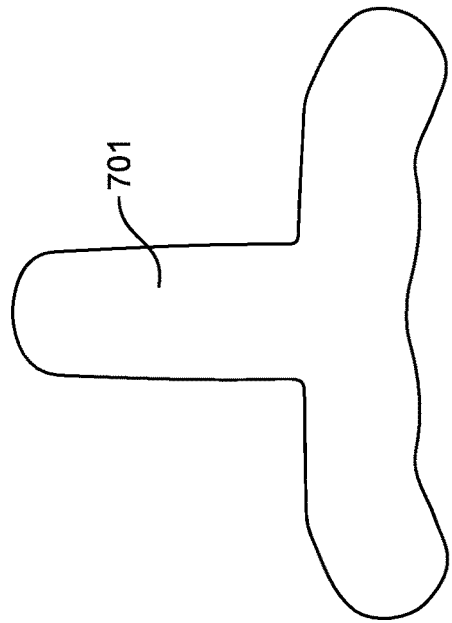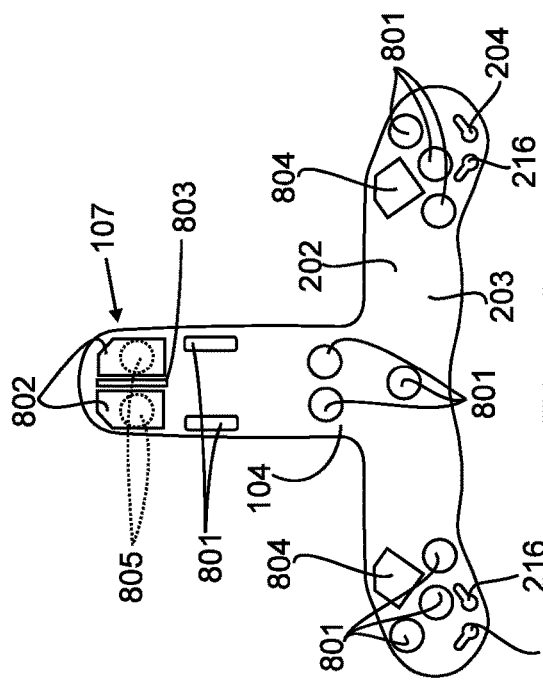

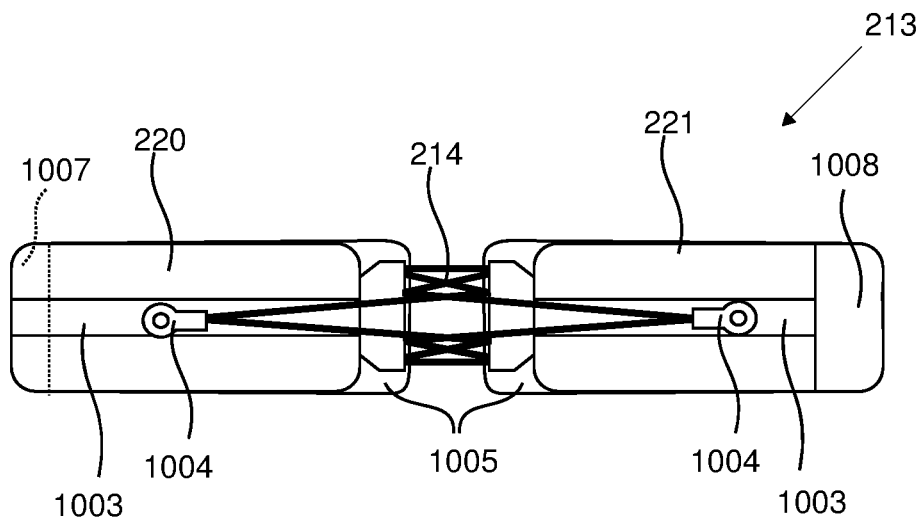
Fig. 10
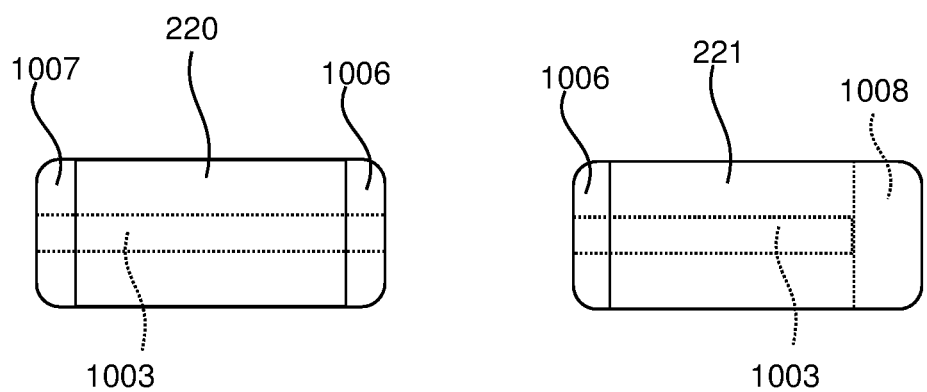
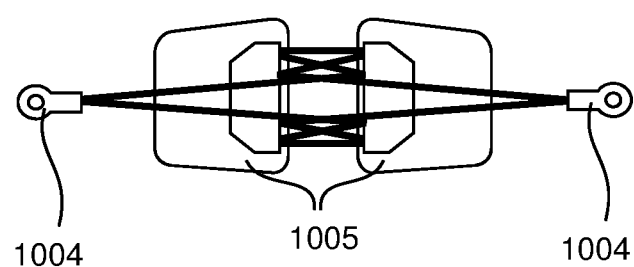
Fig. 11

BRACE AND A METHOD OF FITTING A BRACE

CROSS-REFERENCE TO RELATED APPLICATIONS

This application is a U.S. National Stage of International Application No. PCT/GB2017/051987 filed Jul. 6, 2017, which claims priority from Application 1611789.7 filed on Jul. 6, 2016 in the United Kingdom. The entire contents of these applications are incorporated herein by reference in their entireties.

FIELD OF THE INVENTION

Embodiments of the present invention relate to a brace and a method of fitting a brace. In particular, they relate to a brace and a method of fitting a brace in for the treatment of scoliosis or kyphosis.

BACKGROUND TO THE INVENTION

Braces for treating scoliosis are known that provide a pressing force against the ribs of the wearer. Problems with known braces are that they may be uncomfortable to the wearer and may also restrict movement of the wearer.

BRIEF DESCRIPTION OF VARIOUS EMBODIMENTS OF THE INVENTION

According to various, but not necessarily all, embodiments of the invention there is provided a brace comprising: a belt assembly for location around a body of a user; a strut having a first end and an anchoring location, the first end of the strut being configured to be secured by the belt assembly with the anchoring location spaced from the belt assembly; a first strap for applying a force to the body of the user; a first anchor means configured to retain a first part of the first strap at the anchoring location on the strut; and a second anchor means configured to retain a second part of the first strap at a second anchor location to enable tension to be provided in the first strap.

This provides the advantage that the first strap may be held at a height suitable for applying a force to the torso of a person suffering from scoliosis or kyphosis, without unduly restricting movement of the person.

According to various, but not necessarily all, embodiments of the invention there is provided a method of fitting a brace to a person comprising: positioning a strut along a spine of a person; positioning a belt assembly around a pelvis of the person to provide support for a first end of the strut so that a first anchoring location on the strut is spaced from the belt assembly; and positioning a first strap around the body of the person so that the first strap extends from the first anchor location on the strut to a second anchor location on the belt assembly.

According to various, but not necessarily all, embodiments of the invention there is provided a brace comprising: a main support element comprising a strut defining a first anchoring location and base portion defining a second anchoring location, the base portion having a first part extending to one side of the strut and a second part extending to the other side of the strut; supporting means for supporting the main support element on a user so that the strut extends up from base portion to the first anchoring location; and a first strap; a first anchor means configured to hold a first part of the first strap on the strut; and a second anchor means configured to hold a second part of the first strap to enable tension to be provided in the first strap.

According to various, but not necessarily all, embodiments of the invention there is provided a brace comprising: a belt assembly for location around a body of a user; a strut having a first end and an anchoring location, the first end of the strut being configured to be secured by the belt assembly with the anchoring location spaced from the belt assembly; a first strap for applying a force to the body of the user; a first anchor mechanism configured to retain a first part of the first strap at the anchoring location on the strut; and a second anchor mechanism configured to retain a second part of the first strap at a second anchor location to enable tension to be provided in the first strap.

According to various, but not necessarily all, embodiments of the invention there is provided a brace comprising: a main support element comprising a strut defining a first anchoring location and base portion defining a second anchoring location, the base portion having a first part extending to one side of the strut and a second part extending to the other side of the strut; a belt assembly configured to supporting the main support element on a user so that the strut extends up from base portion to the first anchoring location; and a first strap; a first anchor mechanism configured to hold a first part of the first strap on the strut; and a second anchor mechanism configured to hold a second part of the first strap to enable tension to be provided in the first strap.

According to another embodiment of the invention there is provided a brace comprising: a main support element configured to extend around a pelvic region of a person and to provide anchor locations for straps used to apply forces to the person, the main support element defining a plurality of slots extending around the main support element; a belt portion configured to extend around the main support element for maintaining the main support element in position on the pelvic region of a person, and a plurality of sliding anchor members arranged to slide along the slots, the sliding anchor members being configured to be attached to the belt portion.

In an embodiment each sliding anchor member has two heads connected by a connection means, wherein a first one of the two heads is located on a rear side of the main support element, a second one of the two heads is located on a front side of the main support element and the connection means extends through one of the slots. The first one of the two heads may be provided with hook or loop material to enable attachment to the belt portion.

BRIEF DESCRIPTION OF THE DRAWINGS

For a better understanding of various examples of embodiments of the present invention reference will now be made by way of example only to the accompanying drawings in which:

FIG. 7 shows a main support element 202 assembled with a padded cover 701;

FIG. 8 shows the main support element 202 separately;

FIG. 9 shows the cover 701 separately;

FIG. 10 shows a belt portion 213 of the brace 101 of FIG. 2;

FIG. 11 shows components of the belt portion 213;

DETAILED DESCRIPTION OF VARIOUS EMBODIMENTS OF THE INVENTION

Figure 1A:
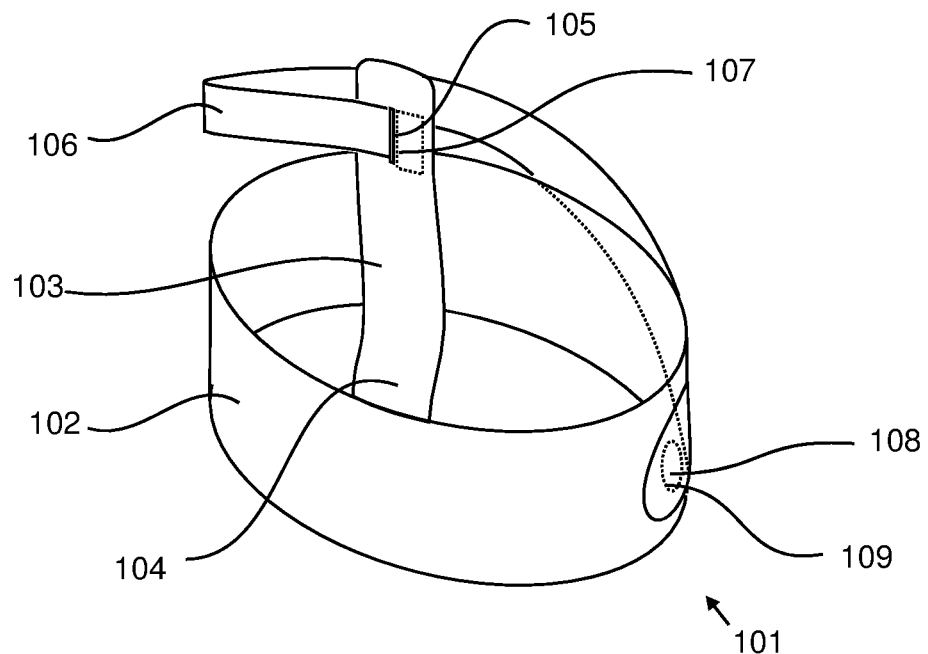
FIGS. 1A and 1B show respectively a schematic perspective view and side view of a brace 101 embodying the present invention.

The Figures illustrate a brace comprising: a belt assembly 102 for location around a body of a user; a strut 103 having a first end 104 and an anchoring location 105, the first end 104 of the strut 103 being configured to be secured by the belt assembly 102 with the anchoring location 105 spaced from the belt assembly 102; a first strap 106 for applying a force to the body of the user; a first anchor means 107 configured to retain a first part of the first strap 106 at the anchoring location 105 on the strut 103; and a second anchor means 108 configured to retain a second part of the first strap 106 at a second anchor location 109 to enable tension to be provided in the first strap.

The second anchor location 109 may be on the belt assembly 102.

Typically, in use the brace is arranged on a user with the belt assembly 102 extending around their pelvis and the strut extending upwards, generally along their spine. The belt assembly 102 is secured to the user to provide a stable base from which the strut extends. The first strap 106 extends from the strut 103 to the belt assembly 102 and by placing first strap 106 in tension, the first strap may be arranged to apply a force to the body of the user in a direction that is normal to the direction in which the first strap extends.

In some embodiments the first strap 106 may be configured to extend around the torso of the user to apply a force to the side of the torso and thereby provide support for a user suffering from scoliosis.

The first strap 106 may comprise a single strap member or two or more strap members joined together to form a chain of straps so that one strap member provides a first portion of the length of the first strap while another strap member provides a different second portion of the length of the first strap.

Thus, as used herein, the phrase "strap member" refers to a strap that may form a part of a longer strap.

Figure 2:
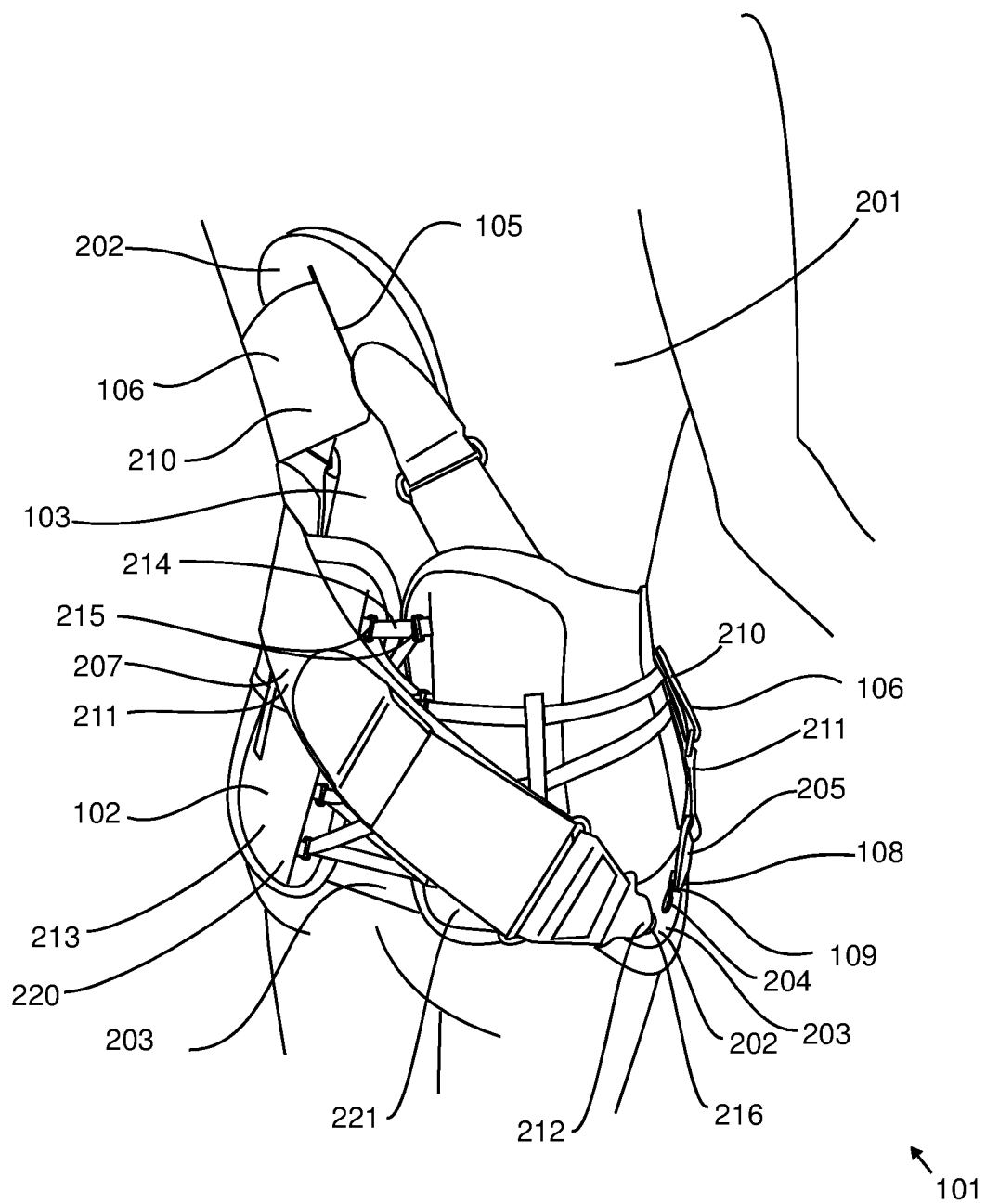
FIG. 2 shows a more detailed rear right view of an example of the brace 101 in use.

In some embodiments, such as the one illustrated in FIG. 2, the first strap 106 may be one of two straps, the second strap extending between different anchor locations on the belt assembly via a pad that is supported by the first strap.

Figure 12B:
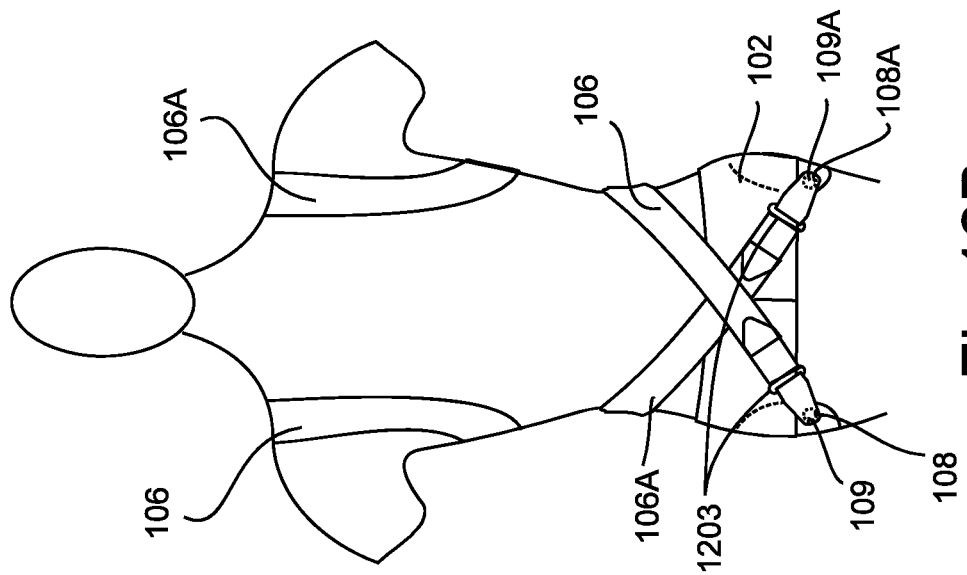
FIGS. 12A and 12B show a rear view and a front view respectively of an alternative brace 101A embodying the present invention.
Figure 12A:
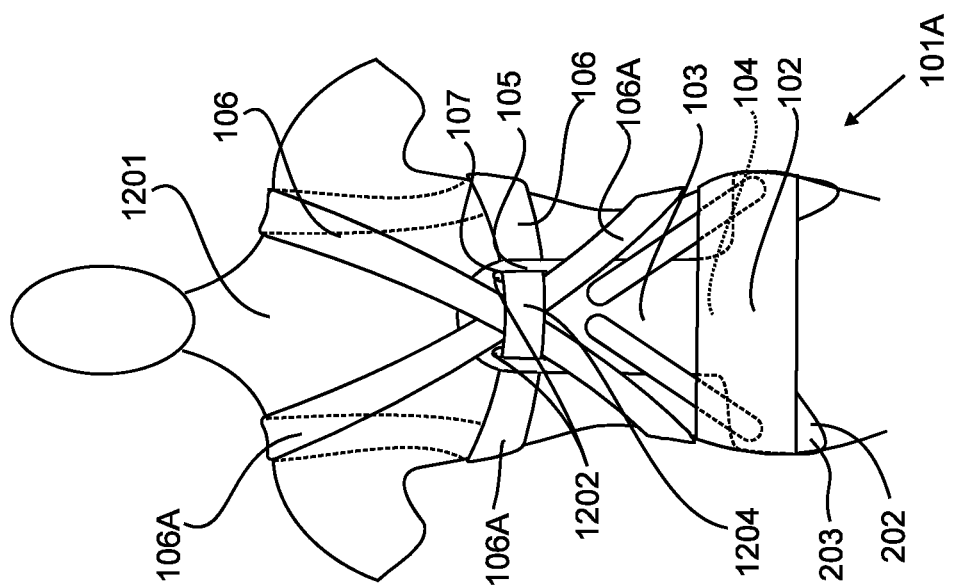

In some embodiments, such as the one illustrated in FIGS. 12A and 12B, the first strap 106 may be one of two straps, each of which extends from the anchoring location 105 on the strut to different anchor locations, on the belt assembly. In such cases the anchor locations on the belt assembly may be located at the front left and front right of the user while the first strap and a second strap extend over respective shoulders of the user. The lengths of the first and second straps may be adjusted to cause the straps to apply pressure to the shoulders of the user. This arrangement may be used for a user who is suffering from kyphosis.

In each case, the strut 103 is formed from a material that is more rigid than the material of the first strap (and the second strap where used). The strut 103 may be formed of a solid sheet of a thermoplastic material, such as high density polyethylene (HDPE), while the first strap (and second strap where present) are formed of a woven material. The woven material of the straps may include elastic fibres and have a woven structure that allows the straps to stretch to enable the user more freedom of movement while maintaining a required force on the user's body.

Figure 1B:
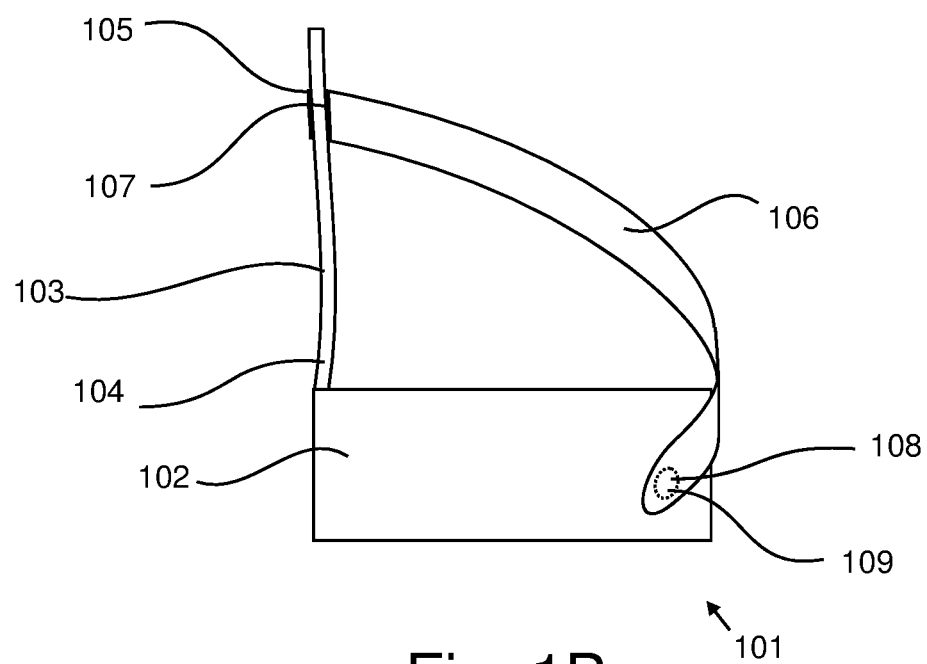

A brace 101 embodying the present invention is shown in a schematic perspective view in FIG. 1A and side view in FIG. 1B. The brace 101 comprises a belt assembly 102 for location around a pelvis of a user. The belt assembly 102 typically has a tightening mechanism (an example of which will be described below with respect to FIG. 2) to allow the belt assembly to be tightened around the pelvis of the user to ensure it rests stably on the user's body.

The brace 101 also comprises a strut 103 having a first end 104 that is attached to the belt assembly 102. The strut 103 defines an anchoring location 105 that is spaced from the belt assembly 102. The brace 101 includes a first anchor means 107 configured to hold a first part of a first strap 106 to the strut 103 at the anchoring location 105. The anchor means 107 may comprise a mechanism that releasably holds the first strap 106 at the strut 103. For example, the anchor means may comprise hook and loop fasteners or other fastening mechanism such as press-stud (or snap fastener), hook and eye, buckle, etc. An example of an arrangement including hook and loop fastening will be described in further detail below.

The brace 101 also includes a second anchor means 108 configured to hold a second part of the first strap 106 at a second anchor location 109 on the belt assembly 102.

As will be described in detail below, the strut 103 may form a part of a main support element comprising the strut and a base portion having a first part extending to one side of the strut and a second part extending to the other side of the strut. In such an arrangement, the base portion of the main support element may form a part of the belt assembly 102 and the second anchor location may be provided on the base portion of the main support element.

Alternatively, the strut 103 may be formed as a separate item to the belt assembly 102 and fixed to the belt assembly, for example by hook and loop fasteners, snap fasteners, or other fastening means that will support the strut in an upright orientation when the belt assembly extends in a substantially horizontal planes.

Figure 3:
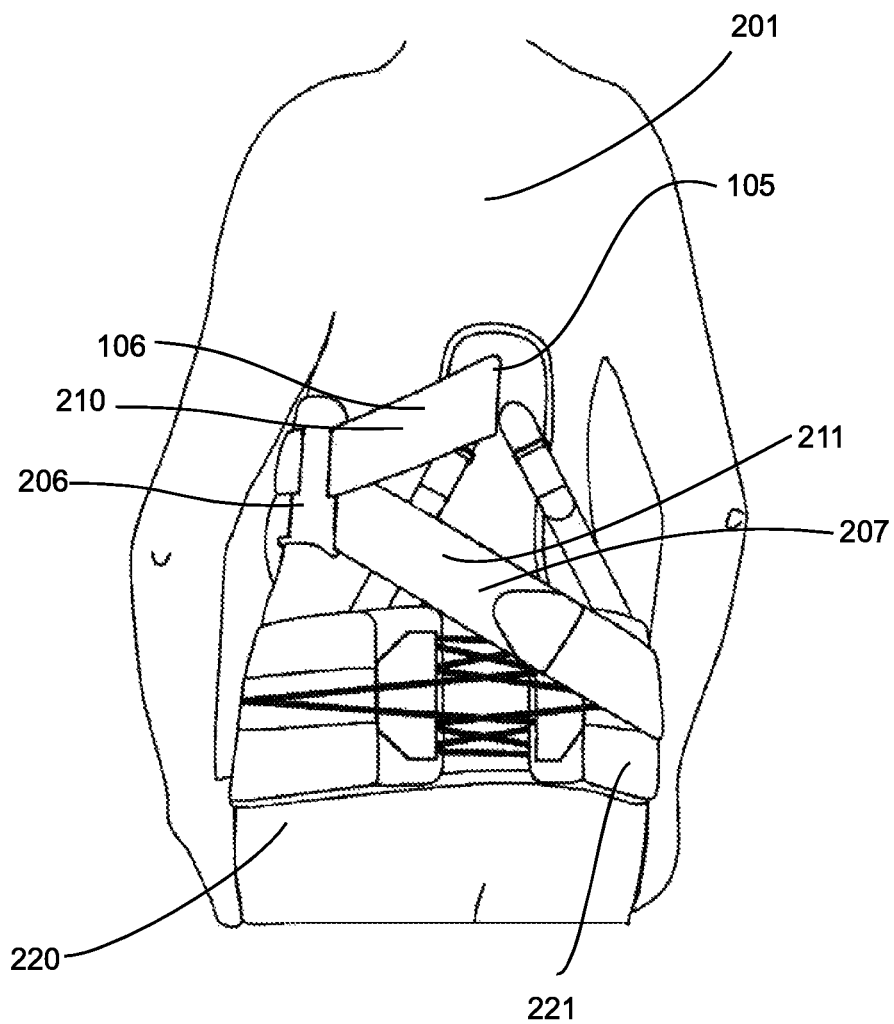
FIG. 3 shows rear left view of the brace 101 of FIG. 2.
Figure 4:
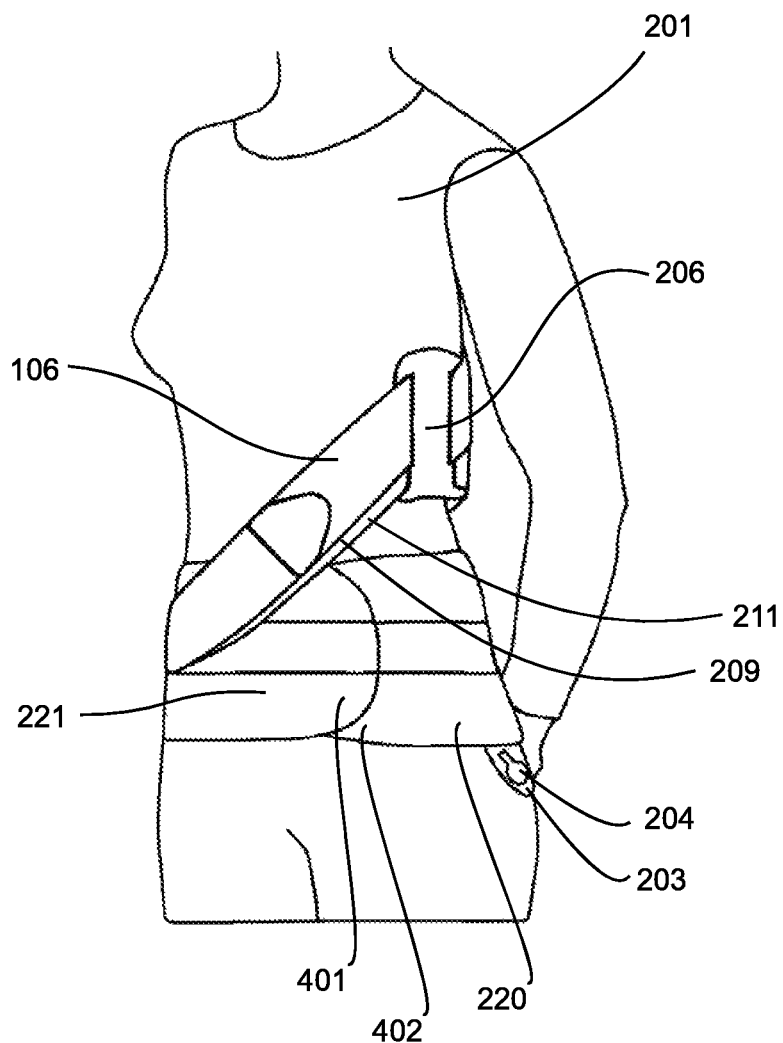
FIG. 4 shows front left view of the brace 101 of FIG. 2.

An example of a brace 101 is shown in further detail, and in use, in FIGS. 2, 3 and 4, which provide rear right, rear left and front left views respectively. The first strap 106 extends from the first anchor location 105 on the strut 103 to the second anchor location 109 on the belt assembly 102. In the present embodiment, the brace 101 comprises a main support element 202 which includes the strut 103 and a base portion 203 that extends from the strut 103 to each side of the strut; the base portion 203 forming a part of the belt assembly 102. Near to at least one of its ends, the base portion 203 defines a hole 204 configured to receive a fastening member provided on an end part 205 of the first strap 106. The hole 204 in co-operation with the fastening member provides an anchor mechanism 108 to enable the first strap 106 to be releasably attached to the belt assembly 102.

In use, the size of the brace 101 fitted to a user will be determined in dependence of the size of the user. In each case, the length of strut 103 will be chosen to extend past the thoracic vertebrae T11 of the user and typically up to between T10 and T7 inclusive.

In the present example, the base portion defines a hole 204 near to each of its two ends. Consequently, the first strap 106 may be arranged to extend clockwise from the strut 103 around the body of the user 201 to the right side of the user where its end is anchored to the base portion 203, as shown in the figures, or, alternatively, the first strap 106 may be arranged to extend anti-clockwise from the strut 103 around the body of the user to the left side of the user where its end is anchored to the base portion 203 at the hole 204 shown in FIG. 4.

The brace 101 may include a pad 206 supported by the first strap 106, as shown in FIGS. 3 and 4, for applying pressure to the side of the ribs of the user. The first strap 106 may be formed of a single continuous piece of material that is extendable between the strut 103 to the anchoring position 109 on the belt assembly 102 via the pad 206. However, in the present embodiment the first strap 106 comprises a first strap member 210 and a portion of a second strap member 211. The first strap member 210 has one end anchored at the strut 103 at the first anchor location 105, it passes through the pad 206 and it has a second end attached to the second strap member 211. The second strap member 211 has a portion that extends beyond the first strap member 210 to the second anchor location 109 on the belt assembly 102. Thus, this portion in combination with the first strap member 210 defines the first strap 106.

In the embodiment of FIGS. 2, 3 and 4, the second strap member 211 has a first section 207 that is configured to extend from a third anchor location 212 on the belt assembly 102 to the pad 206 in a clockwise direction and a second section 209 that is configured to extend from the second anchor location 109 on the belt assembly 102 towards the pad 206 in an anti-clockwise direction. In the present example the second anchor location 109 and the third anchor location 212 are both provided on the main support element 202 adjacent to each other. The means of attachment of the second strap member 211 to the main support element 202 may be similar at each of its ends and as described above. Thus, one end of the second strap member 211 may attach to a first hole 204 while the other end attaches to a similar hole 216.

Advantageously, the pad 206 is supported by an arrangement of straps that extend from the pad in three different directions to respective anchor locations. The first section 207 of the second strap member 211, which extends from the third anchor location 212 around the back of the user to the pad 206, provides forces to the pad 206 that, in co-operation with the first strap 106 enable the position of the pad 206 to be adjusted to a desired height on the user.

The main function of the belt assembly 102 is to provide a stable anchor location 109 for the first strap 106 and to hold the strut 103 in a stable upright configuration so that the first strap 106 may be placed in tension as it extends from the strut 103 around the body of the user 201 to the second anchor location 109. It may also provide a stable third anchor location 212 for attaching the first section 207 of the second strap member 211. As described above, each of these anchor locations 105, 109 and 212 are provided on a main support element 202 that forms the strut 103 and a part of the belt assembly 102. Because the main support element 202 is a relatively stiff sheet of material, tensions in the first strap 106 and the first section 207 of the second strap member 211 do not tend to move the anchor locations 105, 109 and 212 out of position.

To maintain the main support element 202 in position on the user, the belt assembly 102 also comprises a belt portion 213 that encloses the base portion 203 of the main support element 202 during use. Thus the belt portion 213 provides a support means for supporting the main support element on the user.

The belt portion 213 comprises two halves 220 and 221 that are connected end-to-end by laces 214 that pass through eyelets 215 (shown in FIG. 2) on each of the two halves. The laces are arranged so that the user may easily tighten the belt portion by pulling on the laces. Similar lacing arrangements are well known on other belts for orthopedic use.

The other ends 401 and 402 (shown in FIG. 4) of the two halves 220 and 221 of the belt portion 213 are provided with a fastening mechanism to enable the belt portion to form a continuous loop around the user's body. In the present example the fastening mechanism comprises hook and loop fastening but, in alternative embodiments, alternative fastening mechanisms such as hooks and eyes, buckles, or similar mechanisms may be used.

It may be noted that the strut 103 has a relatively broad width (of approximately 100 mm) and a relatively thin thickness (of approximately 2 mm). Thus, the strut 103 is configured to be relatively flexible in directions towards and/or away from the central axis around which the belt assembly 102 is configured to extend and relatively resistant to flexing circumferentially around the axis. Consequently, the strut 103 provides good resistance to bending leftwards and rightwards across the back of the user to provide the anchor location 105 with stability in this direction. However, the strut 103 provides much less resistance to forwards and backwards bending to allow a wearer 201 of the brace 101 to be relatively unrestricted when bending backwards and forwards.

Figure 5:
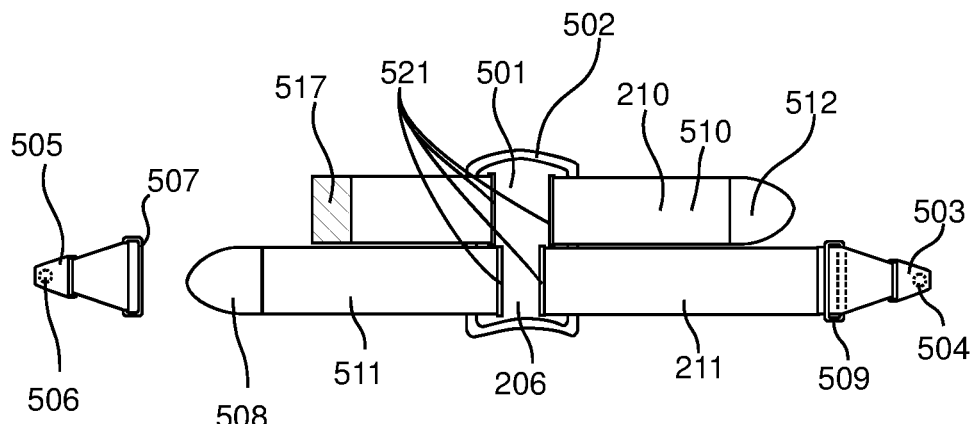
FIG. 5 shows first and second strap members 210 and 211 assembled with a pad 206.
Figure 6:
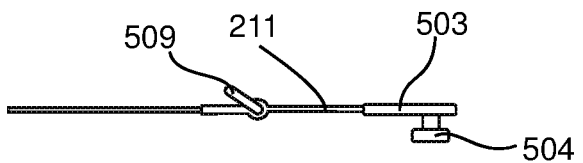
FIG. 6 shows a side view of an end portion of the second strap member 211 of FIG. 5.

The first and second strap members 210 and 211 are shown assembled with the pad 206 in FIG. 5, while a side view of an end portion of the second strap member 211 is shown in FIG. 6.

The pad 206 comprises a relatively rigid member 501 defining slots through which the first and second strap members 210 and 211 are threaded. In the present example each of the two strap members 210 and 211 extend through respective pair of slots. A lining member 502 comprising relatively soft material, such as a polymeric foam, is fixed to one side of the member 501 to provide a padded surface for contacting against the body of the user. In an embodiment the lining member 502 comprises an EVA (ethylene-vinyl acetate) pad covered in a spacer fabric.

In the present example, the main portions 510 and 511 of the first and second strap members 210 and 211 are formed of a material having a loop structure at their surfaces, so that they are able to provide a connection with hook material.

The second strap member 211 is provided at one end with a buckle 503 defining the fastening member 504 for engagement with a hole 204 on the main support element 202. In the present example, the fastening member 504 has the form of a post having an enlarged head. However, it will be appreciated that other shapes for providing a hooking function may be used. It is also possible that the fastening member 504 may be provided on the main support element 202 and the mating hole provided on the buckle 503.

A similar buckle 505 with a fastening member 506 may be provided at the opposite end of the second strap member 211 for connection with the hole 216 on the main support element 202. However, the buckle 505 may be arranged to be releasably attached to the main part of the strap member 211 as illustrated in FIG. 5. In the present example, the buckle 505 is connected to a metal O-ring 507 that defines a slot through which the material of the second strap member 211 may pass. An end portion 508 of the second strap member 211 is provided with a hook material suitable for attaching to the loop material of the main portion 511 of the strap member. Thus, the buckle 505 may be attached to the main portion of the second strap member by looping the main portion of the strap member 211 through the O-ring and fastening the hook material of end portion 508 to the main portion 511. Depending upon the positioning of the end portion 508 along the main portion 511 the overall length of the second strap member may be varied, and consequently during use this enables the tension in the second strap member to be varied.

The second strap member 211 also has a second metal O-ring 509 fixed with respect to the main portion 511 near to its buckle 503. This O-ring 509 is provided to allow attachment of the first strap member 210 to the second strap member 211 to form the above-described first strap 106.

During use a first end portion 517 of the first strap member 210 is attached to the strut 103. A second end portion 512 of the first strap member 210 is provided with hook material, so that the first strap member 210 may be attached to the second strap member 211. This attachment is achieved by passing the end portion 512 through the O-ring 509 of the second strap member, bending the first strap member 210 around the O-ring 509 and attaching the hook material of the end portion 512 to the loop surface of the main portion 510 of the first strap member 210. During use, the tension in the first strap member 210 is adjustable by adjusting the position of the second end portion 512 along the main portion 510.

Figure 15:
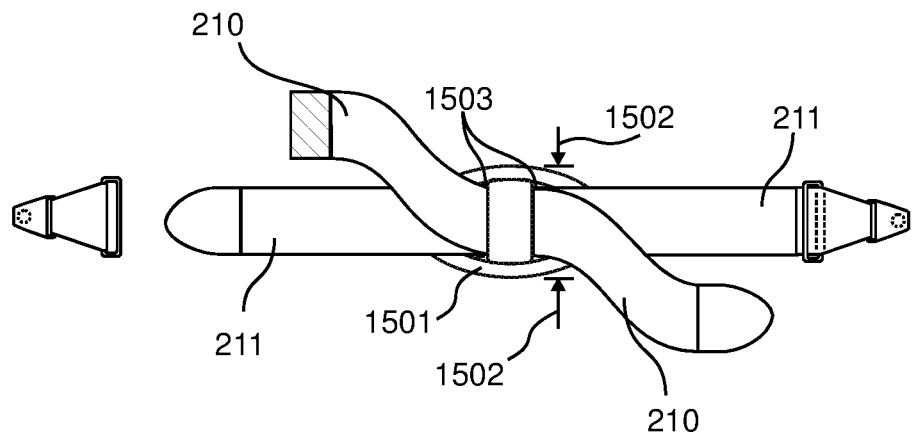
FIG. 15 shows an alternative pad 1501 to pad 206 of FIG. 5.

An alternative pad 1501 to pad 206 is shown in FIG. 15. The pad 1501 has a smaller height (as indicated by arrows 1502) when compared to pad 206 and has a single pair of slots 1503 through which both the first and second strap members 210 and 211 are threaded during use. This enables the pad to be located lower down the body of the user 201, between the ribs and the pelvis. The pad 1501 is otherwise used in the same manner as pad 206.

The main support element 202 is shown in FIG. 7 assembled with a padded cover 701. The main support element 202 and the cover 701 are also shown separately in FIG. 8 and FIG. 9 respectively. The outer surface of the main support element 202 is in view in FIG. 7, whereas the inner surface of the main support element, which is arranged for attachment to the cover 701, is shown in FIG. 8.

As shown in FIG. 8, the main support element 202 comprises the strut 103 which extends from the base portion 203. The base portion 203 comprises first and second parts that extend to either side of the strut. In some examples they may extend to the left and the right from the bottom end 104 of the strut 103 to form an inverted T-shape. In some examples, as shown in FIGS. 7 to 9, the first and second laterally extending parts of the base portion also extend distally to the strut, i.e. a component of the direction of extension extends in a direction opposite to direction in which the strut extends. For example, the first and second parts may additionally extend in a distal or downwards direction (as compared to the upwardly extending strut). Such distal or downwardly extending projections/end sections of the first and second parts (which, in certain examples, may comprise an aperture 204) are shown in FIGS. 4, 12A and 12B.

Figure 16:
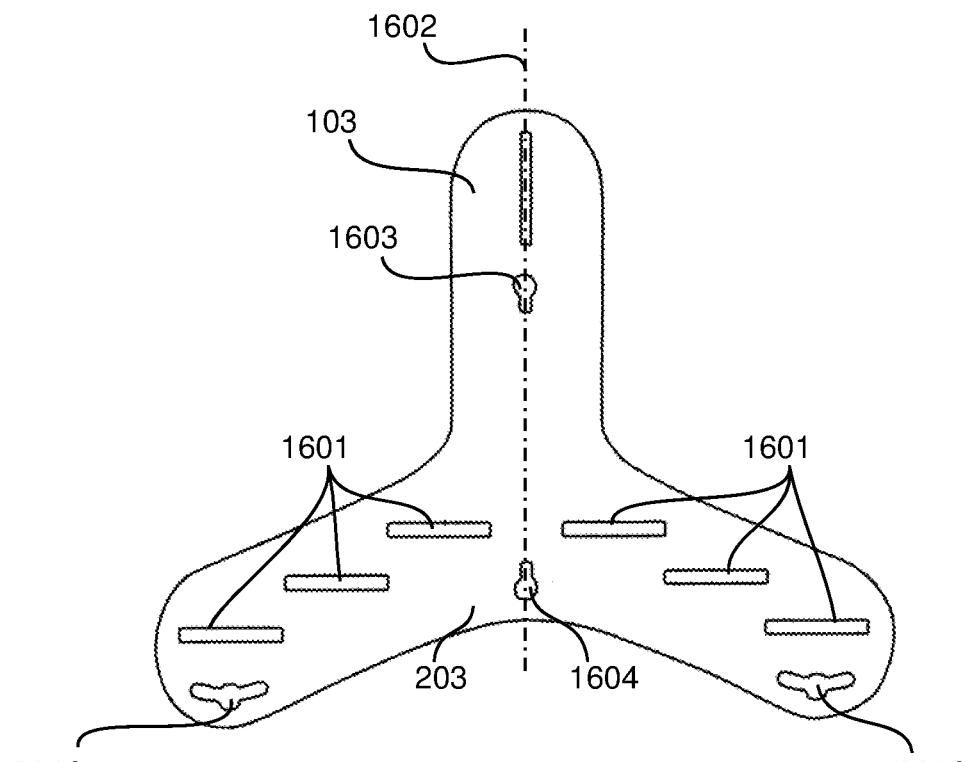
FIG. 16 shows an alternative main support element 202A.
Figure 17A:
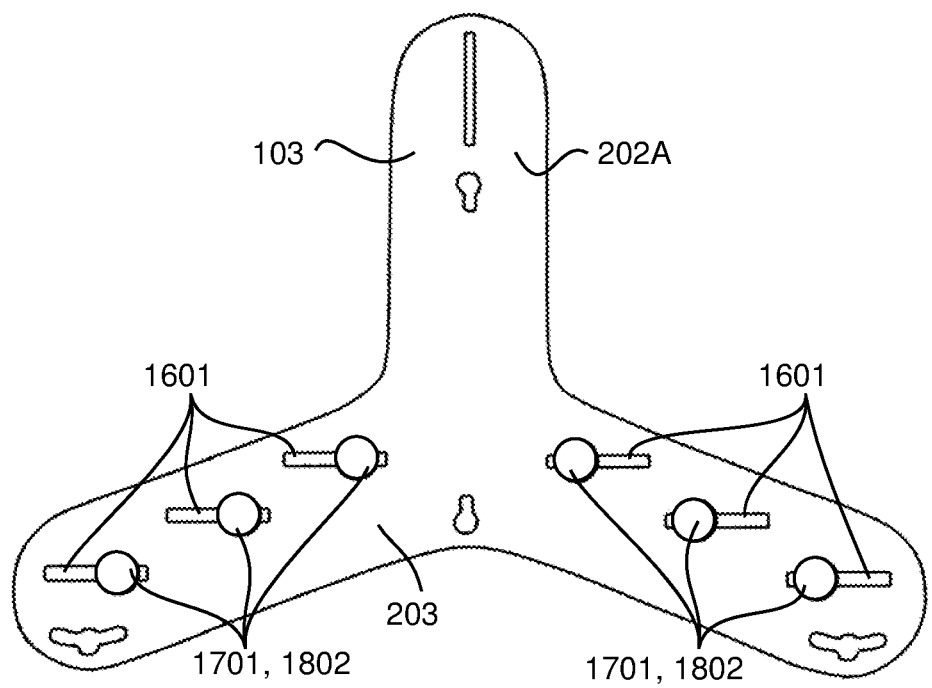
FIGS. 17A and 17B show a rear view and a front view respectively of the main support element.
Figure 17B:
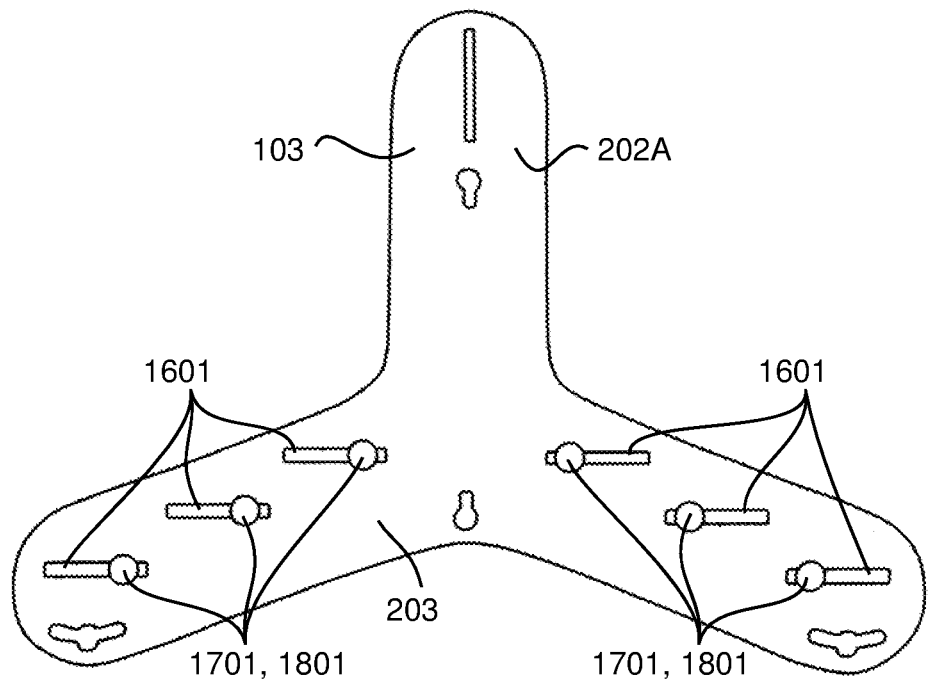

In some examples, as shown in FIGS. 16, 17A and 17B, the base portion comprises first and second parts that extend laterally to either side of the vertically/upwardly extending strut and which also extend in a distal downwards direction away from the strut, i.e. the first and second parts extend in a direction that has a both a lateral/sideways component and a longitudinal/downwards component. In some examples, the first part extends diagonally downwards to one side and the second part extends diagonally downwards to the other side, such that, in effect the: strut, first part and second part of the main support element may form an inverted Y-shapes member.

The first and second parts may extend in one or more of a: lateral, horizontal and circumferential direction (i.e. have a component of the extension direction that extends in a direction perpendicular to the vertically extending strut, e.g. to the left and right of the strut). The first and second parts may be dimensioned to as to extend in such a lateral direction so be configured to wrap around at least a part of a user's body, i.e. so as to at least partially wrap around more than 30% or 50% of the user's hips/hip region.

The first and second parts may additionally extend in one or more of a: longitudinal, vertical and axial direction (i.e. have a component of the extension direction that extends in a direction parallel to the direction of the strut, e.g. a downwards/distal direction away from the strut). The first and second parts may be dimensioned so as to extend in such a longitudinal direction such that, in use when worn by a user, the first and second parts extend beyond or below: the belt assembly and/or the belt portion. The first and second parts may be dimensioned to as to extend in such a direction such that, in use when worn by a user, the first and second parts extend up to or beyond/below a level of user's: lower end of spine, coccyx, pelvis, hip, buttocks and/or trochanter (i.e. such that the first and second parts are adapted to at least partially cover and/or be proximal to: the lower end of a user's spine, the user's coccyx, the user's pelvis, the user's hip, the user's buttocks and/or the user's greater trochanter).

Advantageously, the provision of first and second parts of the main support member that extend both in a lateral and longitudinal directions (i.e. extend both sideways around the user's body and also downwards along a part of the length of the user's body in the hip region) enables the main support member, in effect, to function as a biomechanical lever arm for the application of a lateral/sideways force to the spine of a user by the brace. When the main support is held in position, i.e. via the belt assembly or belt portions, the provision of first and second parts of the main support member that extend both in lateral and longitudinal directions around and along the user's hip region provide stability, mechanical support and rigidity to the brace that resists torsional, twisting or rotational movement of the brace and the main support member during use (i.e. that may otherwise occur due to tension applied to the first strap coupled to the main support member at an anchor point on an upper distal end portion of the strut). The laterally and longitudinally extending first and second parts of the support member are configured to, when in use and worn by a user, restrict movement of the support member and brace in the lateral/ circumferential direction as well as restrict rotational movement of the support member about a central region of the base portion.

The strut 103 of the support member is configured to permit/not restrict a user leaning forwards and backwards, i.e. the strut is configured to be flexible in such forward and backward directions towards and away from the central axis. This allows a user 201 of the brace 101 to be relatively unrestricted when bending backwards and forwards, which may increase user comfort. Advantageously, the brace may provide a degree of freedom of movement of the user's torso, i.e. not restricting a user from leaning forwards and bending backwards, whist providing a sideways pressing force against the ribs of the user (e.g. for the treatment of scoliosis) and resistance to the brace twisting/rotating leftwards/rightwards across the back of the user.

The holes 204 provided near to each end of the base portion 203 of the main support element 202 are provided with a keyhole shaped contour so that the enlarged head of the fastening member 504 may pass through the wide end of the hole 204. The narrow part of the hole 204 is dimensioned to allow the fastening member 504 to slide into it but sufficiently narrow to retain the enlarged head of the fastening member 504.

A hole 216 is provided adjacent to each of the holes 204 for receiving the fastening member 506 provided at the end of the second strap member 211. The holes 216 may be configured with a keyhole shape in a similar manner to holes 204.

The cover 701 is included to provide padding between the back of the user and the main support element 202. The cover 701 has a surface suitable for attachment to hook material, i.e. to provide hook and loop fastening. In the present example the cover 701 comprises velour material. A plurality of self-adhesive patches 801 of hook material are adhered to the main support element 202 enabling the cover to be attached.

Patches 802 of self-adhesive hook material 802 are attached to the main support element 202 on either side of a slot 803 in the main support element. The slot 803 and one or other of the patches 802 provides the first anchor means 107 for holding the first strap 106 on the strut 103. To achieve this, the end portion 517 of the first strap member 210 is passed through the slot and fixed to the hook material of the patch 802.

In the present example, additional patches 804 of self-adhesive hook material are provided on the base portion 203 of the main support element 202, either side of, and spaced from, the strut 103. Also patches of self-adhesive hook material 805 are provided on the strut 103 near to its free end 702. Two stabilizing straps 703 may be provided that have ends configured to attach to the patches 804 and 805. Thus, as shown in FIG. 7, two stabilizing straps 703 may be attached to the strut 103 near to its free end at patches 805 and to the base portion 203 at the location of the patches 804. The stabilizer straps 703 further assist the strut 103 to maintain its required orientation. In an alternative arrangement, only a single stabilizing strap 703 is used. In such cases, the single stabilizing strap 703 is arranged to extend from the opposite side of the strut than the first strap 106. I.e. if the first strap 106 is arranged to extend leftwards from the strut 103, the stabilizing strap 703 is arranged to extend rightwards, and if the first strap 106 is arranged to extend rightwards from the strut 103, the stabilizing strap 703 is arranged to extend leftwards. In this way, the bending moment on the strut caused by the first strap 106 may be counteracted by the tension in the stabilizing strap 703.

The stabilizing straps 703 may be placed in tension and thereby produce a compressive force in the strut 103. The strut is formed of a flexible material and so it is able to curve under the compressive force. Furthermore, a lower portion 710 (indicated by a dashed outline) of the strut 103 may be pre-shaped to encourage bending of the strut in this lower portion, so that the lower portion 710 flexes towards the wearer 201. Thus, the strut 103 may be provided with a shape that provides lumbar support and the shape may be adjusted by adjusting flexing in the strut by adjustment of the tension in the stabilizing straps 703.

To facilitate adjustment of tension in the stabilizing straps 703, the stabilizing straps 703 may be provided with a mechanism for adjusting their length. For example, the stabilizing straps 703 may be formed of two parts as shown in FIG. 7. A first part 704 may include an O-ring 705 through which the second part 706 may be looped. An end portion 707 of the second part 706 may be provided with hook material to enable it to be attached to different positions of a main section of the second part 706 and thereby provide different amounts of tension in the stabilizing strap 703.

In an alternative example, instead of fixing the cover 701 to one side of the main support element 202, a cover is provided that is formed of two layers of material that envelope the main support element. The cover may be formed of a material (such as velour) suitable for attachment to hook material and the ends of the strap member 210 and stabilizer straps 703 may be provided with a patch of hook material for fixing to the cover. Openings may be provided in the cover to enable access to the holes 204, 216, or other features, provided on the main support element for anchoring the end of the first strap 106 and/or the second strap member 211.

The belt portion 213 is shown in FIG. 10 and components of the belt portion 213 are shown in FIG. 11. As mentioned above, the belt portion 213 comprises two halves 220 and 221 connected together by laces 214. The two halves 220 and 221 may be formed of a textile material such as a spacer fabric. Each of the two halves 220 and 221 is provided with a strip 1003 of hook receptive material (i.e. material defining loops) on one side, while ends of the laces 214 are provided with a tab 1004 formed of hook material. Therefore, during use the laces may be tightened and held tight by fixing the tabs 1004 to the strips 1003.

The laces 214 are threaded through eyelets located on two connecting portions 1005 fixed to respective ends of the two halves 220 and 221. The connecting portions 1005 may be permanently fixed to the two halves 220 and 221, or alternatively, as shown in FIG. 11, the halves 220 and 221 may be provided with strips 1006 of hook material along one edge to enable attachment of a respective connecting portion 1005 to each of the two halves.

A strip of hook material 1007 is also provided on one of the halves 220 along an edge that is opposite to that where its connecting portion 1005 is located. Similarly, a strip of loop material 1008 is provided on the other one of the halves 221 along an edge that is opposite to where its connecting portion 1005 is located. The strips of hook material 1007 and loop material 1008 enable the two halves 220 and 221 to be fastened together around the body of a person.

An alternative main support element 202A to that of FIG. 8 is shown in FIG. 16. The main support element 202A may be generally configured in the same manner as main support element 202A. However it differs in the following ways.

The main support element 202A has a base portion 203 that defines a plurality of slots 1601. The strut 103 extends from the base portion 203 along a center line 1602, and the slots 1601 extend along parallel lines that are perpendicular to the center line 1602. In an example, the slots have a length of about 75 mm and a width of about 7 mm.

The slots 1601 provide a means for enabling the two halves 220 and 221 of the belt portion 213 to be attached to the main support element 202A, so that they are able to slide in the direction of the slots but prevented from sliding perpendicular to the direction of the slots. Thus, the two halves 220 and 221 may slide along the slots when the belt portion 213 is tightened, but they are prevented from moving up or down out of their correct position in which they surround the base portion 203.

Figure 18:
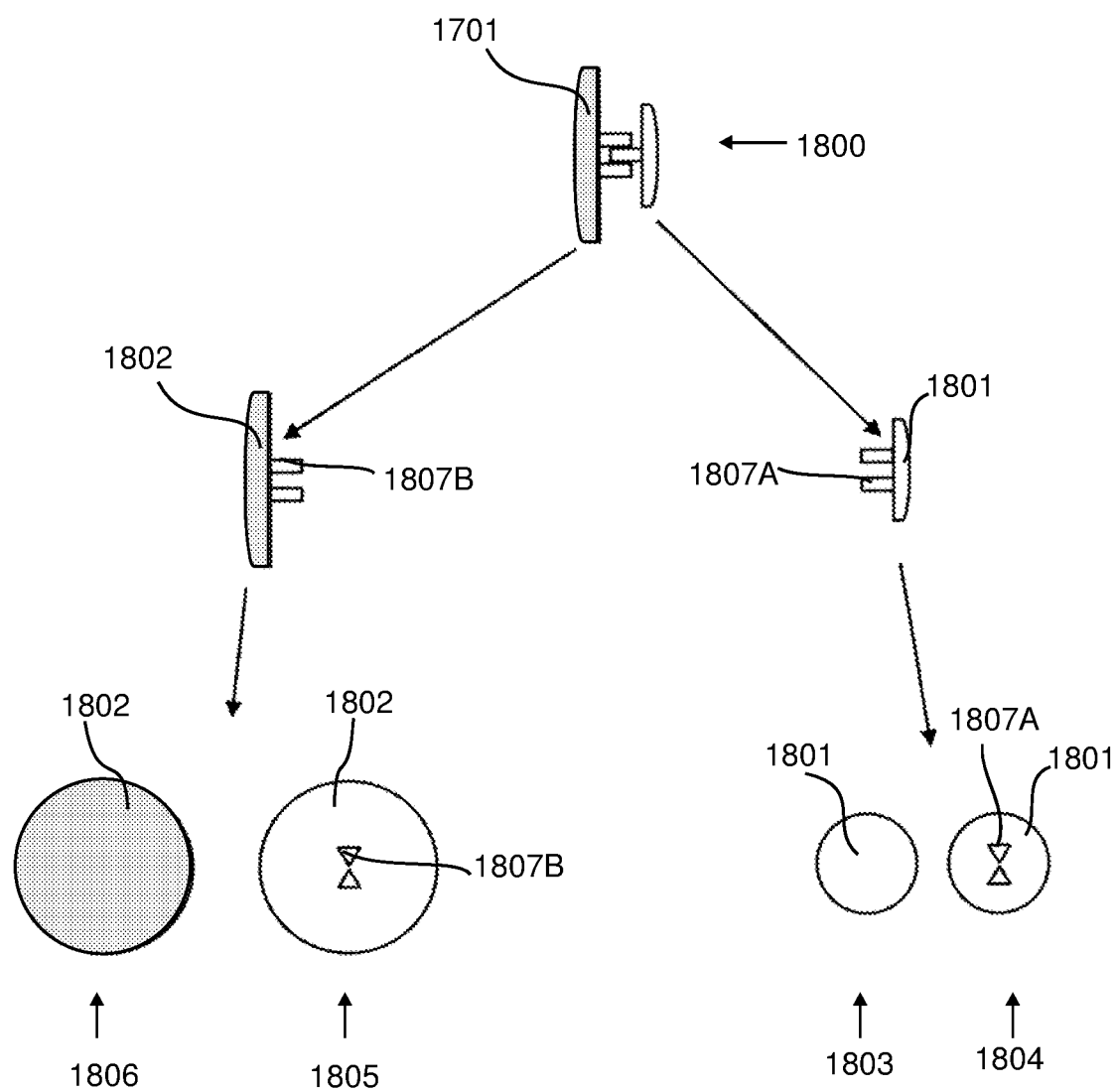
FIG. 18 shows a side view at 1800 of a sliding anchor member 1701 and also various views of the two constituent parts 1801 and 1802 of the sliding anchor member 1701.

To attach the two halves 220 and 221 of the belt portion 213 to the main support element 202A, each of the slots 1601 is provided with a sliding anchor member 1701 as shown in the rear view of FIG. 17A and the front view of FIG. 17B. An example of a sliding anchor member 1701 is shown in a side view at 1800 in FIG. 18. FIG. 18 also shows various views of the two constituent parts 1801 and 1802 of the sliding anchor member 1701.

A sliding anchor member 1701 in the present example comprises a rivet formed of a plastics material. The rivet 1701 is formed of two parts: a smooth headed part 1801 and a hook headed part 1802 that has a head covered in hook material for forming a hook and loop connection. Front and rear views of the smooth headed part 1801 are shown at 1803 and 1804 respectively, and front and rear views of the hook headed part 1802 are shown at 1805 and 1806 respectively.

The rear of the smooth headed part 1801 and the front of the hook headed part are provided with connecting means 1807A and 1807B to enable the two parts 1801 and 1802 to be fixed together. The connecting means may comprise a ratchet mechanism, as is known in the art, or other known connecting mechanisms, such as a screw threaded connection or a spring clip connection.

The connecting means 1807A, 1807B are dimensioned so that they are able to extend through one of the slots 1601, and be fastened together. That is, the hook headed part 1802 may be positioned at the rear of the main support element 202A with its connecting means 1807B extending into a slot 1601 and the smooth headed part 1802 may be positioned at the front of the main support element 202A with its connecting means 1807A extending into the same slot 1601 and connected to the connecting means 1807B of the hook headed part 1802. In this way, a sliding anchor member 1701 may be fixed into each of the slots 1601. The connecting means 1807A and 1807B of a sliding anchor member 1701 are dimensioned to enable the sliding anchor member 1701 to slide along its slot 1601 but prevent its movement perpendicular to the length of the slot.

A sliding anchor member 1701 may be made from a conventional plastic rivet that has hook material attached to the head of one of its two parts. The hook material on the head of the hook headed part 1802 may be fixed to the head of the rivet by an adhesive. Alternatively, the hook material may be sewn to a second piece of material so that the hook material and the second piece of material form a pocket that encloses the head of the rivet.

The inner surface of the two halves 220 and 221 of the belt portion 213 may be formed of a material, such as velour, that is receptive to hook material. I.e. The inner surface of the two halves 220 and 221 of the belt portion 213 (which may be seen in FIG. 11) may be formed of a material that is capable of forming a hook and loop connection with the hook material of the sliding anchor members 1701. Thus, after fixing a sliding anchor member 1701 within each of the slots 1601, as shown in FIGS. 17A and 17B, the belt portion 213 may be attached to the main support element 202 by bringing its inner surface into contact with the hook material of the sliding anchor members 1701.

In the present example, as shown in FIG. 17A, three sliding anchor members 1701 are provided in respective slots 1601 on the base portion 203 on each side of the strut 103. Thus, one half 220 of the belt portion 213 may be attached to three of the sliding anchor members to the left of the strut 103 and the other half 221 of the belt portion 213 may be attached to the three sliding anchor members to the right of the strut 103. Because the two halves 220 and 221 of the belt portion 213 are mounted on the sliding anchor members 1701, the two halves may be slid with respect to the main support element 202A to enable tightening of the belt portion using the laces 214.

The main support element 202A of FIG. 16 also differs from the main support element 202 of FIG. 8 in that it has been provided with an additional anchor hole 1603 on the strut 103 and a second anchor hole 1604 on the base portion 203 on the center line 1602 of the strut 103. The holes 1603 and 1604 may be provided with a keyhole shape as shown in FIG. 16. The holes 1603 and 1604 may be used to anchor a tensioning strap (not shown) that has fastening members at either of its two ends that are configured to hook into the holes 1603 and 1604. The fastening members of the tensioning strap may be similar to the fastening members 504 of the second strap member 211 as described above and shown in FIGS. 5 and 6. The tensioning strap may also be provided with a means of adjusting its length, which may also be similar to the mechanism described for the second strap member 211. Consequently, with the tensioning strap attached to the holes 1603 and 1604, the length of the tensioning strap may be shortened to place it under tension. This also has the effect of placing the strut under tension and causing it to curve inwards to towards the wearer and provide lumbar support. (This may be appropriate when the main support element 202A is used in the brace 101A described below with respect to FIGS. 12A and 12B for the treatment of kyphosis, or hyperkyphosis.)

The hole 1603 on the strut may also be used to anchor one or two stabilizing straps 703 that are provided with a fastening member (like fastening member 504 of the second strap member 211) rather than being provided with hook and loop fastening 705. The opposite end of such a stabilizing strap may be attached to the base portion of the main support element 202A using a hook and loop connection as discussed with respect to FIG. 8, or may be connected to an end portion of the second strap, for example by hoop and loop connectors.

The main support element 202A also differs from the main support element 202 in that it only has a single hole 204A at each end of its base portion 203. Also, the holes 204A have a different shape in that they have a relatively narrow slot on each side of a central circular hole. Thus, the holes 204A are arranged to receive two fastening members of 504 of the second strap member 211, so that one fastening member 504 resides in one of the narrow slots and the other fastening member resides in the other one of the narrow slots.

A rear view and a front view of an alternative brace 101A embodying the present invention is shown in FIGS. 12A and 12B respectively. Like the brace 101, the brace 101A comprises a belt assembly 102 which supports a strut 103 at one end 104 of the strut 103. The belt assembly 102 of brace 101A is configured to extend around the pelvis of a wearer 1201, in the same manner as described above for brace 101, with the strut 103 extending upwards, generally along the spine of the wearer. The brace 101A comprises a first strap 106 having a first end attached to the strut 103 at a first anchor location 105. The opposite end of the first strap 106 is releasably attachable to the belt assembly 102 at an anchor location 109 by a second anchor means 108.

The brace 101A differs from the brace 101 in that it has a second strap 106A that has a first end attached to the strut 103 and a second end attachable to the belt assembly 102 at an anchor location 109A by a further anchor means 108A. The anchor locations 109 and 109A may be symmetrically positioned on the belt assembly to the left and right sides of the user, and the anchor means 108 and 108A may be similar to the anchor means 108 described above for the brace 101.

The first strap 106 and the second strap 106A may each be formed of several strap members, so that each strap member only extends along a portion of the full length of the strap 106 or 106A. Alternatively the straps 106 and 106A may each comprise a single strap member. Furthermore, the first strap 106 and the second strap 106A may be formed of the same continuous length of strap material that has a central point anchored on the strut as shown in FIG. 12A. For example, the strut 103 may be provided with a pair of slits 1202 through which half of the strap material is passed, so that one half provides the first strap 106 and the other half provides the second strap 106A. The first and second straps 106 and 106A may be anchored by a hook and loop fastening mechanism or alternative anchoring means as described above for brace 101. Alternatively, where the first and second straps 106 and 106A are formed of a single length of material, they may be retained by the strut 103 only by being threaded through the slits 1202.

In an embodiment, the strut 103 is provided with just one central slit instead of the two slits 1202, and the first and second straps 106 and 106A each have an end portion that passes through the central slit and is attached to the strut by a hook and loop fastening mechanism.

The first and second straps 106 and 106A may be formed in a similar way as described above in respect of the first and second strap members 210 and 211 of brace 101, and they may each comprise an elasticated strap material. However, the straps 106 and 106A of FIGS. 12A and 12B will generally be longer than those of FIG. 2 as necessitated by the route they are required to take over the body of the wearer.

The brace 101A may be generally formed in substantially the same manner as the brace 101 of FIGS. 2 to 4 and as described with respect to FIGS. 5 to 11. The strut 103 may form a part of a main support element 202 (as shown in FIG. 8) or 202A (as shown FIGS. 16, 17A and 17B) having a base portion 203 that forms a part of the belt assembly 102. Ends of the first strap 106 and the second strap 106A may be provided with fastening members as described above that are arranged to engage with features (such as holes 204 or 204A) on the main support element 202 or 204A at anchor locations 109 and 109A.

During use, the belt portion 102 is located around the pelvis of the user and may be tightened by a lace arrangement (not shown in FIG. 12A or 12B) such as described above with regard to brace 101.

As shown in FIGS. 12A and 12B, the first strap 106 may be routed from the strut 103 around the right side of the torso of the wearer 1201 and over the right shoulder to return to the strut 103. It may then extend around the left side of the abdomen and be anchored at the right side anchor location 109. In a symmetrical manner, the second strap 106A may be routed from the strut 103 around the left side of the torso of the wearer and over the left shoulder to return to the strut 103. It may then extend around the right side of the abdomen and be anchored at the left side anchor location 109A.

In the embodiment of FIG. 12A, the first and second straps are formed of a single length of material that has a middle section 1204 extending between the slots 1202 in the strut 103, and mid-portions of the first and second straps are anchored to the strut by being positioned between the middle section 1204 and the strut 103.

Tension in the first strap 106 and the second strap 106A provide forces on the shoulders of the wearer that tend to pull the shoulders back toward the strut 103. Thus, the brace 101A is suitable for use with a person suffering from kyphosis (or hyperkyphosis).

Means for adjusting the length of the first strap 106 and second strap 106A may be provided so that tension in the first and second straps may be adjusted. For example, the end of the straps 106 and 106A may be provided with an O-ring arrangement 1203 like that of the second strap member 211 described above, so that the length of the straps may be adjusted.

It may be noted that, as described above with regard to brace 101, the strut 103 may be provided with a degree of flexibility in the forward and backward direction. Consequently the user has some freedom to bend forwards and backwards while wearing the brace 101A. In addition, the user is not rigidly fixed to the strut 103 and therefore the user is relatively free to bend sideways.

Figure 13:
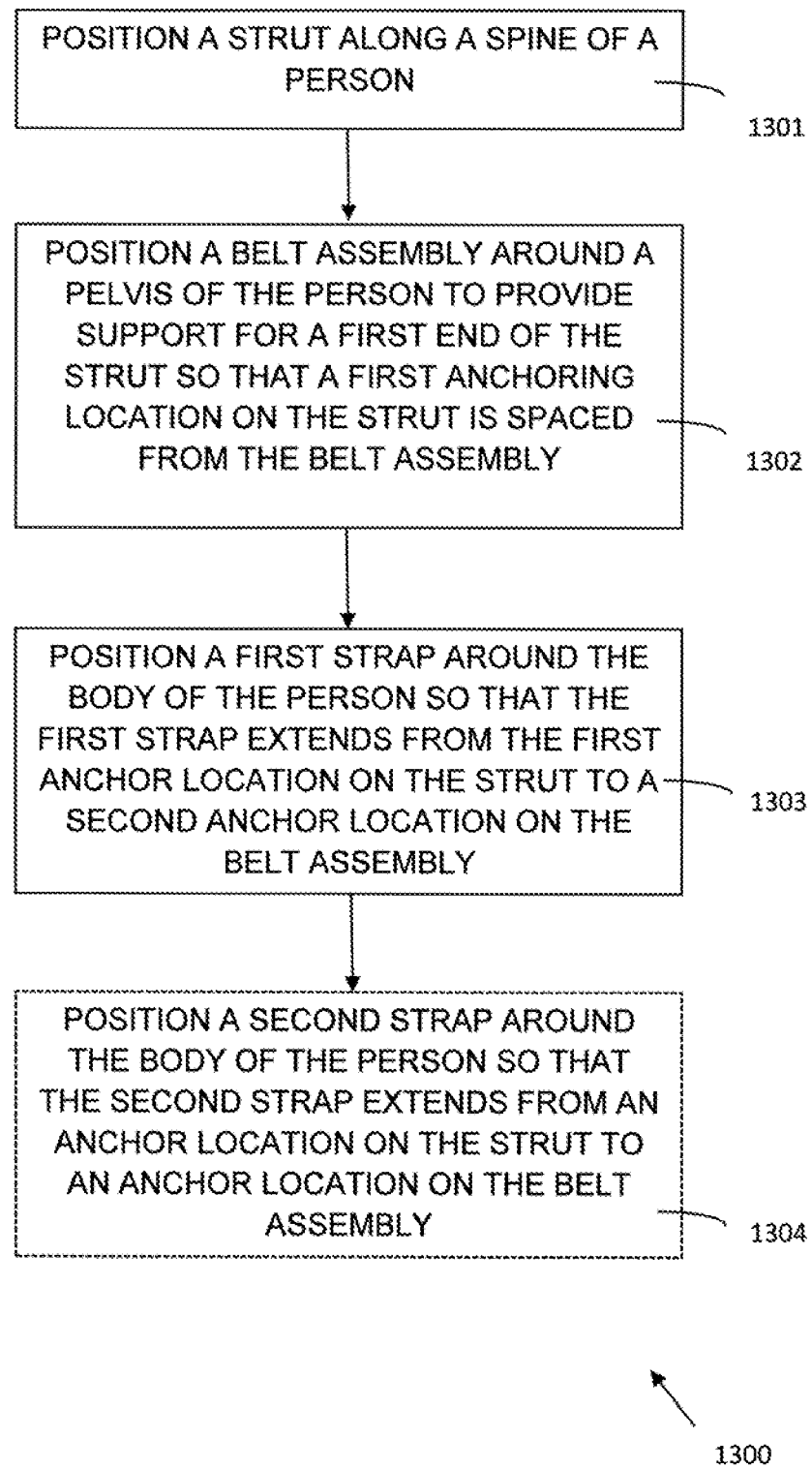
FIG. 13 shows a flowchart outlining a method 1300 of fitting a brace to a person.

A method 1300 of fitting a brace to a person is outlined in the flowchart shown in FIG. 13. The method 1300 comprises positioning a strut, such as strut 103, along a spine of a person at block 1301. A belt assembly is then positioned around a pelvis of the person at block 1302 to provide support for a first end of the strut, so that a first anchoring location on the strut is spaced from the belt assembly. At block 1303, a first strap is then positioned around the body of the person so that the first strap extends from the first anchor location on the strut to a second anchor location on the belt assembly. Typically, the first strap is anchored to the strut before the strut is positioned at block 1301, but alternatively, a releasable mechanism for retaining the first strap on the strut may be used, in which case the first strap may be anchored to the strut after the belt assembly is fitted at block 1302.

Typically, the first strap is anchored to the second anchor location on the belt assembly after the first strap is positioned around the body of the person, using a releasable anchor mechanism at the second anchor location.

Optionally, at block 1304 a second strap is positioned around the body of the person so that the second strap extends from an anchor location on the strut to an anchor location on the belt assembly. In an example, the second strap is located over one shoulder of the wearer, while the first strap is located over the other shoulder, as described above with reference to FIGS. 12A and 12B.

Figure 14:
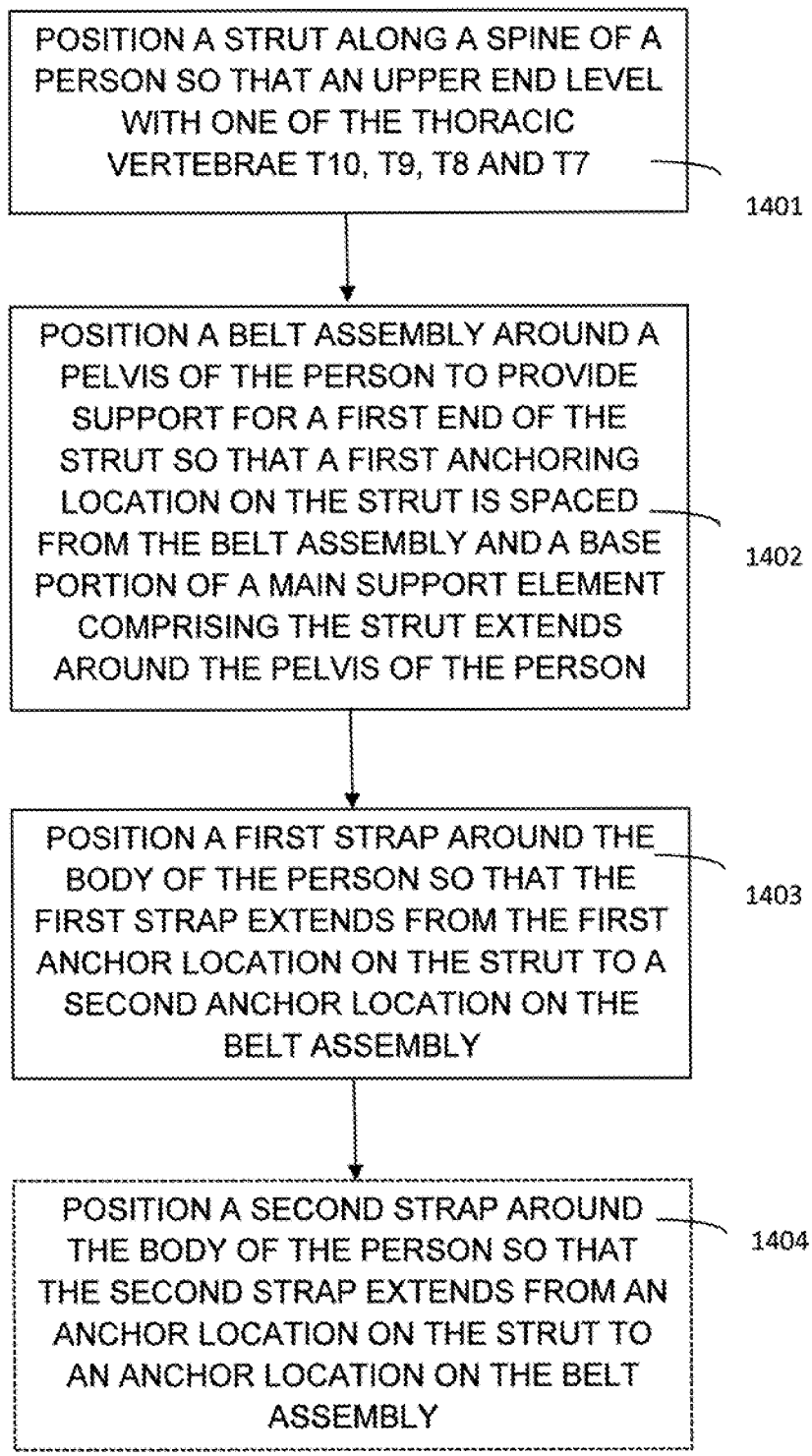
FIG. 14 shows a flowchart outlining a method 1400 of fitting a brace to a person.

A method 1400 of fitting a brace to a person is outlined in the flowchart shown in FIG. 14. The method 1400 is similar to method 1300 of FIG. 13. However, at block 1401, the method 1400 comprises positioning a strut along a spine of a person so that an upper end of the strut is level with one of the thoracic vertebrae T10, T9, T8 and T7. Such a height of strut enables the first strap to apply a force, for example via a pad 206, to ribs of the wearer of the brace.

A belt assembly is then positioned around a pelvis of the person at block 1402 to provide support for a first end of the strut, so that a first anchoring location on the strut is spaced from the belt assembly. In the present method, the strut forms a part of a main support element, such as element 202 shown in FIG. 8, which has a base portion that extends to the left and right from the first end (i.e. the lower end) of the strut. As shown in FIG. 14 at block 1402, when positioning the belt assembly, the base portion of the main support element is made to extend around the pelvis of the person.

At block 1403, a first strap is then positioned around the body of the person so that the first strap extends from the first anchor location on the strut to a second anchor location on the belt assembly. Optionally, at block 1404 a second strap is positioned around the body of the person so that the second strap extends from an anchor location on the strut to an anchor location on the belt assembly. In an example, the second strap is located over one shoulder of the wearer, while the first strap is located over the other shoulder, as described above with reference to FIGS. 12A and 12B.

With regard to the flowcharts of FIGS. 13 and 14, the particular order to the blocks does not necessarily imply that there is a required or preferred order for the blocks and the order and arrangement of the block may be varied.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed:

1. A brace comprising:
   a belt assembly for location around a body of a user;
   a main support element comprising a strut and a base portion, the strut having a first end and an anchoring location, the first end of the strut being configured to be secured by the belt assembly with the anchoring location spaced from the belt assembly, the base portion having a first part extending to one side of the strut and a second part extending to the other side of the strut, wherein an end of the first part extends beyond the belt assembly, and wherein an end of the second part extends beyond the belt assembly; and
   a first strap for applying a force to the body of the user;
   a first anchor means configured to retain a first part of the first strap at the anchoring location on the strut; and
   a second anchor means configured to retain a second part of the first strap at a second anchor location to enable tension to be provided in the first strap wherein the second anchor location is on the belt assembly;
   wherein the belt assembly is configured to extend around a central axis of the belt assembly and the strut is configured to flex towards and/or away from the central axis and to resist flexing circumferentially around the axis.

2. A brace according to claim 1, wherein the first strap comprises a first strap member connected to a second strap member so that the first strap member provides a first portion of a length of the first strap and the second strap member provides a different portion of the length of the first strap; and
   optionally wherein the second strap member extends from the second anchor location to a third anchor location on the belt assembly.

3. A brace according to claim 1, further comprising a pad for applying pressure to the body of the user, the pad being configured to be supported by the first strap; and optionally wherein the pad is supported by an arrangement of straps that extend from the pad in at least three different directions to respective anchor locations.

4. A brace according to claim 1, wherein a first part of the belt assembly extends to one side of the strut and a second part of the belt assembly extends to the other side of the strut.

5. A brace according to claim 1, wherein the main support element includes a feature to provide the second anchor means; and
   optionally wherein the feature comprises a hole in the main support element for receiving an attachment member on the first strap.

6. A brace according to claim 1, wherein the main support element defines a plurality of slots extending around the main support element; the belt assembly comprises a belt portion configured to extend around the main support element for maintaining the main support element in position on the pelvic region of the user; and the brace comprises a plurality of sliding anchor members arranged to slide along the slots in the main support element, the sliding anchor members being configured to be attached to the belt portion.

7. A brace according to claim 1, wherein the strut is configured to extend along the spine of the user during use.

8. A brace according to claim 1, wherein the second anchor location is on the end of the first or second part which extends beyond the belt assembly.

9. A brace according to claim 1, wherein the first part and the second part of the main support element;
   comprise end sections that extend in a direction opposite to a direction in which the strut extends; and/or
   additionally extend in an axial direction.

10. A brace according to claim 1, wherein the strut, the first part and the second part of the main support element form an inverted Y-shape.

11. A brace according to claim 1, wherein the first and second parts are dimensioned such that, in use when worn by the user, the first and second parts extend at least up to one or more of a level of the user's: lower end of spine, coccyx, pelvis, hip, buttocks and/or trochanter; and/or
   configured such that, in use when worn by the user, the first and second parts at least partially cover one or more of the user's: lower end of spine, coccyx, pelvis, hip, buttocks and/or trochanter.

12. A brace according to claim 1, wherein the brace comprises stabilizer straps configured to extend from the strut to the belt assembly to stabilize a positioning of the strut and resist flexing of the strut circumferentially around the axis; and
   optionally wherein the stabilizer straps are configurable to produce compressive force in the strut and the strut is configured to curve under the compressive force.

13. A method of fitting the brace according to claim 1 to the user, comprising:
   positioning the strut along a spine of the user;

positioning the belt assembly around a pelvis of the user to provide support for the first end of the strut so that the first anchoring location on the strut is spaced from the belt assembly; and positioning the first strap around the body of the user so that the first strap extends from the first anchor location on the strut to the second anchor location.

14. A method as claimed in claim 13, further comprising positioning the base portion around the pelvis of the user.

15. A method as claimed in claim 13 further comprising positioning the base portion so as to partially cover and/or be proximal to one or more of: the lower end of the user's spine, the user's coccyx, the user's pelvis, the user's hip, the user's buttocks and/or the user's greater trochanter.

16. A method as claimed in claim 13, wherein the positioning of the strut along a spine of the user comprises positioning an upper end of the strut to be level with one of the thoracic vertebrae T10, T9, T8 and T7.

17. A brace comprising:

a main support element comprising a strut defining a first anchoring location and base portion defining a second anchoring location, the base portion having a first part extending to one side of the strut and a second part extending to the other side of the strut;

supporting means for supporting the main support element on a user so that the strut extends up from the base portion to the first anchoring location;

a first strap;

a first anchor means configured to hold a first part of the first strap on the strut;

a second anchor means configured to hold a second part of the first strap to enable tension to be provided in the first strap, wherein the second anchor means is on the base portion of the main support element;

wherein an end of the first part extends beyond the supporting means;

wherein an end of the second part extends beyond the supporting means; and wherein the supporting means is configured to extend around a central axis of the supporting means and the strut is configured to flex towards and/or away from the central axis and to resist flexing circumferentially around the axis.

* * * * *